United States Patent
Okajima et al.

(10) Patent No.: US 11,318,258 B2
(45) Date of Patent: May 3, 2022

(54) SYRINGE

(71) Applicants: TAKEDA PHARMACEUTICAL COMPANY LIMITED, Osaka (JP); YOSHINO KOGYOSHO CO., LTD., Tokyo (JP); ARTE CORPORATION, Tokyo (JP)

(72) Inventors: Kiyoshi Okajima, Takahagi (JP); Yuki Imanishi, Ibaraki (JP); Jiichi Arai, Osaka (JP); Yusuke Chuma, Osaka (JP)

(73) Assignees: TAKEDA PHARMACEUTICAL COMPANY LIMITED, Osaka (JP); YOSHINO KOGYOSHO CO., LTD., Tokyo (JP); ARTE CORPORATION, Tokyo (JP)

( * ) Notice: Subject to any disclaimer, the term of this patent is extended or adjusted under 35 U.S.C. 154(b) by 162 days.

(21) Appl. No.: 16/500,004

(22) PCT Filed: Mar. 13, 2018

(86) PCT No.: PCT/JP2018/009689
§ 371 (c)(1),
(2) Date: Oct. 1, 2019

(87) PCT Pub. No.: WO2018/186119
PCT Pub. Date: Oct. 11, 2018

(65) Prior Publication Data
US 2020/0061303 A1    Feb. 27, 2020

(30) Foreign Application Priority Data
Apr. 5, 2017   (JP) .............................. JP2017-075178

(51) Int. Cl.
*A61M 5/32*   (2006.01)
*A61M 5/34*   (2006.01)

(52) U.S. Cl.
CPC ............ *A61M 5/3202* (2013.01); *A61M 5/34* (2013.01)

(58) Field of Classification Search
CPC .............. A61M 5/3202; A61M 5/3275; A61M 5/3293; A61M 5/34
See application file for complete search history.

(56) References Cited

U.S. PATENT DOCUMENTS 7,001,363 B2 * 2/2006 Ferguson ............ A61M 5/3275
604/198
10,357,618 B2 * 7/2019 Okajima ............. A61M 5/3204
(Continued)

FOREIGN PATENT DOCUMENTS

CN   101674772 A   3/2010
JP   2001-515767 A  9/2001
(Continued)

OTHER PUBLICATIONS

English Abstract of JP 2003-52822, from Espacenet (https://worldwide.espacenet.com/patent/search/family/019076681/publication/JP2003052822A?q=pn%3DJP2003052822A). (Year: 2021).*
(Continued)

*Primary Examiner* — Nathan R Price
*Assistant Examiner* — Tasnim Mehjabin Ahmed
(74) *Attorney, Agent, or Firm* — Nath, Goldberg & Meyer; Joshua B. Goldberg (57) ABSTRACT

The present invention suppresses the amount of fluid pushed out from an injection needle when confirming whether air has been pushed out of the injection needle. Provided is a syringe that comprises: a cylinder 20; an injection needle 22; a needle base 24; an injection needle cover 26; and a plunger rod 28. The needle base 24 communicates between the inside of the cylinder 20 and the inside of the injection needle 22. The injection needle cover 26, when extended
(Continued)

from a folded state, surrounds the injection needle 22. The injection needle cover 26 comprises an injection needle surrounding part. The injection needle surrounding part has at least one cutout 130 in a section facing the needle base 24 and covering the needle base, such that the needle base 24 can be identified from the outside.

4 Claims, 9 Drawing Sheets

(56) References Cited

U.S. PATENT DOCUMENTS

| | | | | |
|---|---|---|---|---|
| 2001/0039401 | A1* | 11/2001 | Ferguson | A61M 5/158 604/263 |
| 2003/0004465 | A1* | 1/2003 | Ferguson | A61B 5/150671 604/198 |
| 2008/0319346 | A1* | 12/2008 | Crawford | A61B 5/1545 600/577 |

FOREIGN PATENT DOCUMENTS

| | | |
|---|---|---|
| JP | 2003-52822 A | 2/2003 |
| JP | 2003-514596 A | 4/2003 |
| JP | 2005521537 A | 7/2005 |
| JP | 2009-535105 A | 10/2009 |
| WO | 2016/098861 A1 | 6/2016 |
| WO | 2016098861 A1 | 6/2016 |

OTHER PUBLICATIONS

Search Report dated Sep. 11, 2020 issued in corresponding to European Application No. 18780572.6.
First Office Action dated May 8, 2021, for corresponding Chinese application No. 201880023851.4.
Notice of Reasons for Refusal dated Oct. 8, 2021 corresponding to Japanese application No. 2019-511114.

* cited by examiner

SYRINGE

TECHNICAL FIELD

The present invention relates to a syringe.

BACKGROUND ART

Patent Document 1 discloses a safe injection needle cover which is extendable with respect to an injection needle. The injection needle cover is formed by a plurality of rigid segments serially connected by a plurality of intersegment hinges. The rigid segments are disposed around the injection needle and folded upon each other during a medical procedure. The rigid segments are extended at the end of the medical procedure. The extended injection needle cover protectively sheathes the injection needle.

Patent Document 2 discloses an injection needle cover. The injection needle cover includes a base part, a base hinge, a connecting position fitting space forming part, a connecting hinge, and an injection needle surrounding part. The base part is fixed to an injection needle protruding face to surround an injection needle. The injection needle protruding face is a face of a syringe where the injection needle protrudes from a cylinder. The syringe includes the cylinder and the injection needle protruding from the cylinder. The base hinge is a hinge provided to the base part. The connecting position fitting space forming part is connected to the base part by the base hinge in such a manner as to turn about a base axis. The base axis is an axis orthogonal to a central axis of the injection needle. The connecting position fitting space forming part has a moment receiving part that receives moment about the base axis as a turning center. The connecting position fitting space forming part forms a space where a portion of the injection needle connected to the cylinder is to become fitted. The connecting hinge is a hinge provided to the connecting position fitting space forming part. The injection needle surrounding part is connected to the connecting position fitting space forming part by the connecting hinge in such a manner as to turn about a connecting axis. The connecting axis is an axis parallel to the base axis. The injection needle surrounding part includes paired base-side wall parts, a cylinder part, paired tip-end-side wall parts, and an injection needle contact part. The paired base-side wall parts form a base-side axial space where a portion of the injection needle is to become fitted. The cylinder part is continuous from the paired base-side wall parts. The cylinder part forms an intra-cylinder space communicating with the base-side axial space. The paired tip-end-side wall parts are continuous from the cylinder part. The paired tip-end-side wall parts form a tip-end-side axial space where a tip end of the injection needle is to become fitted such that the tip-end-side axial space communicates with the intra-cylinder space. The paired tip-end-side wall parts are disposed on an opposite side of the cylinder part from the paired base-side wall parts such that the base-side axial space and the tip-end-side axial space are aligned with each other. The injection needle contact part is disposed at such a position as to come in contact with the injection needle when the base hinge opens. The position is in one of the base-side axial space and the intra-cylinder space. The injection needle contact part has a force receiving part and a connecting part. The force receiving part receives a force from the injection needle when the force receiving part comes in contact with the injection needle. The connecting part connects the paired base-side wall parts or the cylinder part to the force receiving part. The force receiving part has an easy sliding part. The easy sliding part is disposed in an area adjacent to the injection needle. The area adjacent to the injection needle is an area on a side of a portion, which faces the injection needle after the injection needle becomes fitted in the base-side axial space and the tip-end-side axial space, closer to the tip-end-side axial space. The easy sliding part slides along the injection needle more easily than the following edge, if the edge slides along the injection needle. The edge has an equal coefficient of static friction to a surface of the connecting part and crosses the injection needle.

Patent Document 3 discloses a safety shield apparatus. The safety shield apparatus includes a safety shield. The safety shield includes a distal segment having a distal end and a proximal end, a proximal segment having a distal end and a proximal end, and a retention member. The proximal end of the distal segment is pivotally connected to the distal end of the proximal segment. The retention member is pivotally secured to the proximal end of the proximal segment. The retention member includes an opening. The opening is dimensioned to be received to be able to slide about a nose of a medical needle device. The retention member includes the opening such that the distal segment and the proximal segment of the safety shield are manually movable from a retracted position to an advanced position to shield a needle supported on the medical needle device.

Patent Document 4 discloses a safety apparatus. The safety apparatus is for shielding a medical needle such that the medical needle is accessible again. The safety apparatus includes a medical needle assembly, a medical shield, and a guide. The medical needle assembly includes a hollow bore cannula. The bore cannula is fixed in a hub. The bore cannula has a sharpened distally disposed tip to form the medical needle.

PRIOR ART DOCUMENTS

Patent Documents

Patent Document 1: Japanese Translation of PCT Publication No. 2001-515767

Patent Document 2: International Publication No. 2016/098861

Patent Document 3: Japanese Translation of PCT Publication No. 2009-535105

Patent Document 4: Japanese Translation of PCT Publication No. 2003-514596

SUMMARY OF THE INVENTION

Problem to be Solved by the Invention

Each of the inventions disclosed in Patent Documents 1 to 4 has a disadvantage that a large amount of fluid is pushed out from the injection needle when confirming whether air has been pushed out of the injection needle.

The present invention has been made to solve the problem. It is an objective of the present invention to provide a syringe capable of suppressing an amount of fluid pushed out from an injection needle when confirming whether air has been pushed out of the injection needle.

Solutions to the Problem

As a result of hard studies on the above-described problem, the present inventors have found that, by instantly making a visual identification of entry of fluid stored in a syringe into an injection needle, it is possible to suppress an amount of fluid pushed out from the injection needle and have made the present invention. The invention is as follows.

A syringe according to a first aspect of the invention includes:
- a cylinder in which fluid is stored;
- an injection needle that discharges the fluid;
- a needle base that connects the injection needle to the cylinder and communicates between an inside of the cylinder and an inside of the injection needle; and
- an injection needle cover that is attached to the cylinder and, when extended from a folded state, surrounds the injection needle, wherein the cylinder includes
- an outer cylinder that forms a storage space in which the fluid is stored, and
- a cylinder tip which is provided to protrude from one end of the outer cylinder, to which the needle base is connected, and which forms a communication passage that communicates between the inside of the injection needle and the storage space, the injection needle cover includes
- a base part that is fixed to surround the cylinder tip,
- a base hinge that is a hinge provided to the base part,
- an injection needle surrounding part through which the needle base is inserted and which faces the base part in the folded state of the injection needle cover and which surrounds the injection needle when the injection needle cover is extended,
- a fitting space forming part that is connected to the base part by the base hinge in such a manner as to turn about a base axis and forms a space in which the injection needle surrounding part is to become fitted, the base axis being an axis orthogonal to a central axis of the injection needle,
- a connecting hinge that connects the injection needle surrounding part to the fitting space forming part such that the injection needle surrounding part is movable about a connecting axis which is an axis parallel to the base axis, and
- a facing connecting part that connects the base part and the injection needle surrounding part with the injection needle surrounding part facing the base part, the needle base is transparent or translucent, and the injection needle surrounding part has at least one cutout in a part of the injection needle surrounding part facing the needle base and covering the needle base such that the needle base can be identified from outside when the base part and the injection needle surrounding part are connected by the facing connecting part in the folded state of the injection needle cover.

The cylinder has the outer cylinder. The outer cylinder forms the storage space. The fluid is stored in the storage space. The cylinder has the cylinder tip as well. The cylinder tip is provided to protrude from the one end of the outer cylinder. The needle base is connected to the cylinder tip. The cylinder tip forms the communication passage. The communication passage communicates between the inside of the injection needle and the storage space. The needle base communicates between the inside of the cylinder and the inside of the injection needle. In this way, the fluid stored in the cylinder can be discharged through the injection needle. The base part of the injection needle cover is fixed in such a manner as to surround the cylinder tip. The base hinge is provided to the base part. The fitting space forming part is connected to the base part by the base hinge in such a manner as to turn about the base axis. The fitting space forming part forms the space in which the injection needle surrounding part is to become fitted. The injection needle surrounding part is connected to the fitting space forming part by the connecting hinge in such a manner as to turn about the connecting axis. The facing connecting part connects the base part and the injection needle surrounding part with the injection needle surrounding part facing the base part. The needle base is transparent or translucent. The cutout provided to the injection needle surrounding part makes it possible to identify the needle base from outside when the base part and the injection needle surrounding part are connected by the facing connecting part in the folded state of the injection needle cover. In this way, it possible to identify an inside of the communication passage in the transparent or translucent needle base from outside when the base part and the injection needle surrounding part are connected by the facing connecting part. Because the inside of the communication passage in the needle base can be identified from outside, it is possible to instantly make a visual identification of entry of the fluid stored in the syringe into the injection needle. The instant visual identification of the entry of the fluid makes it possible to instantly stop the operation for pushing out the fluid. Because the operation for pushing out the fluid can be stopped instantly, it is possible to suppress an amount of fluid pushed out from the injection needle. As a result, it is possible to suppress the amount of fluid pushed out from the injection needle when confirming whether the air has been pushed out of the injection needle.

In addition to the structures according to the first aspect, in the syringe according to a second aspect of the invention,
the cutout has paired cutout inner wall parts that form the single cutout and face each other, and
an arcuate bottom part that is disposed between the paired cutout inner wall parts and continuous from the paired cutout inner wall parts.

The cutout of the injection needle surrounding part has the arcuate bottom part. The arcuate bottom part is disposed between the paired cutout inner wall parts. The arcuate bottom part is continuous from the paired cutout inner wall parts. The arcuate bottom part provided to the cutout, as compared with a straight bottom of a cutout, makes stress concentration less likely to occur, when the injection needle surrounding part receives a force in such a direction as to narrow an opening of the cutout. If the stress concentration becomes less likely to occur, the injection needle surrounding part can withstand a larger force.

In addition to the structures according to the second aspect, in the syringe according to a third aspect of the invention,
a minimum value of a distance between the paired cutout inner wall parts in a direction orthogonal to the central axis of the injection needle is greater than or equal to a maximum value of an opening width of the arcuate bottom part in the direction orthogonal to the central axis of the injection needle.

If the minimum value of the distance between the paired cutout inner wall parts in the following direction is greater than or equal to the maximum value of the opening width of the arcuate bottom part in this direction, a view of the needle base is less likely to be obstructed by an edge of the cutout than when the minimum value of the former is smaller than the maximum value of the latter. The direction is orthogonal to the central axis of the injection needle when the base part and the injection needle surrounding part are connected by the facing connecting part in the folded state of the injection needle cover. If the view of the needle base is less likely to be obstructed by the edge of the cutout, it is easier to visually identify whether the fluid has entered the injection needle than when the view is likely to be obstructed.

In addition to the structures according to the first aspect, in the syringe according to a fourth aspect of the invention,
the cutout has
paired cutout inner wall parts that form the single cutout and face each other, and
a linear bottom part that is disposed between the paired cutout inner wall parts and inclined to be deeper when seen from an edge of one of the cutout inner wall parts, and
the linear bottom part has a flat face that extends along a direction orthogonal to the central axis of the injection needle when the base part and the injection needle surrounding part are connected by the facing connecting part with the injection needle surrounding part facing the base part.

If the flat face provided to the linear bottom part extends along the direction orthogonal to the central axis of the injection needle when the base part and the injection needle surrounding part are connected by the facing connecting part with the injection needle surrounding part facing the base part, the view of the needle base is less likely to be obstructed by parts close to opposite ends of the linear bottom part than when the flat face is not orthogonal to but inclined with respect to the central axis of the injection needle. If the view of the needle base is less likely to be obstructed, it is easier to visually identify whether the fluid has entered the injection needle than when the view is likely to be obstructed.

Effect of the Invention

According to the aspects of the present invention, it is possible to suppress the amount of fluid pushed out from the injection needle when confirming whether the air has been pushed out of the injection needle.

EMBODIMENTS OF THE INVENTION

The embodiments of the present invention will be described below with reference to the drawings. In the following description, the same parts will be provided with the same reference signs. The same parts have the same names and functions. Therefore, the same parts will not be described in detail repeatedly.

First Embodiment

[Description of Structure of Syringe]

Figure 1:
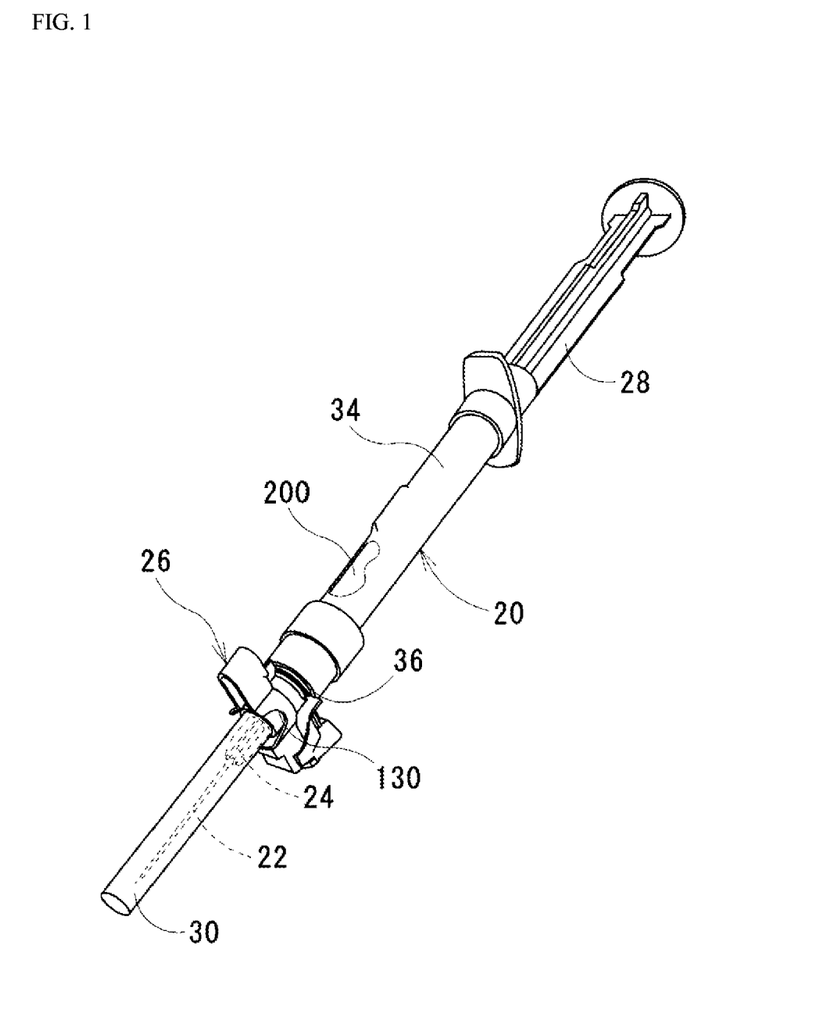
FIG. 1 is a view of a syringe according to a first embodiment of the present invention.
Figure 2:
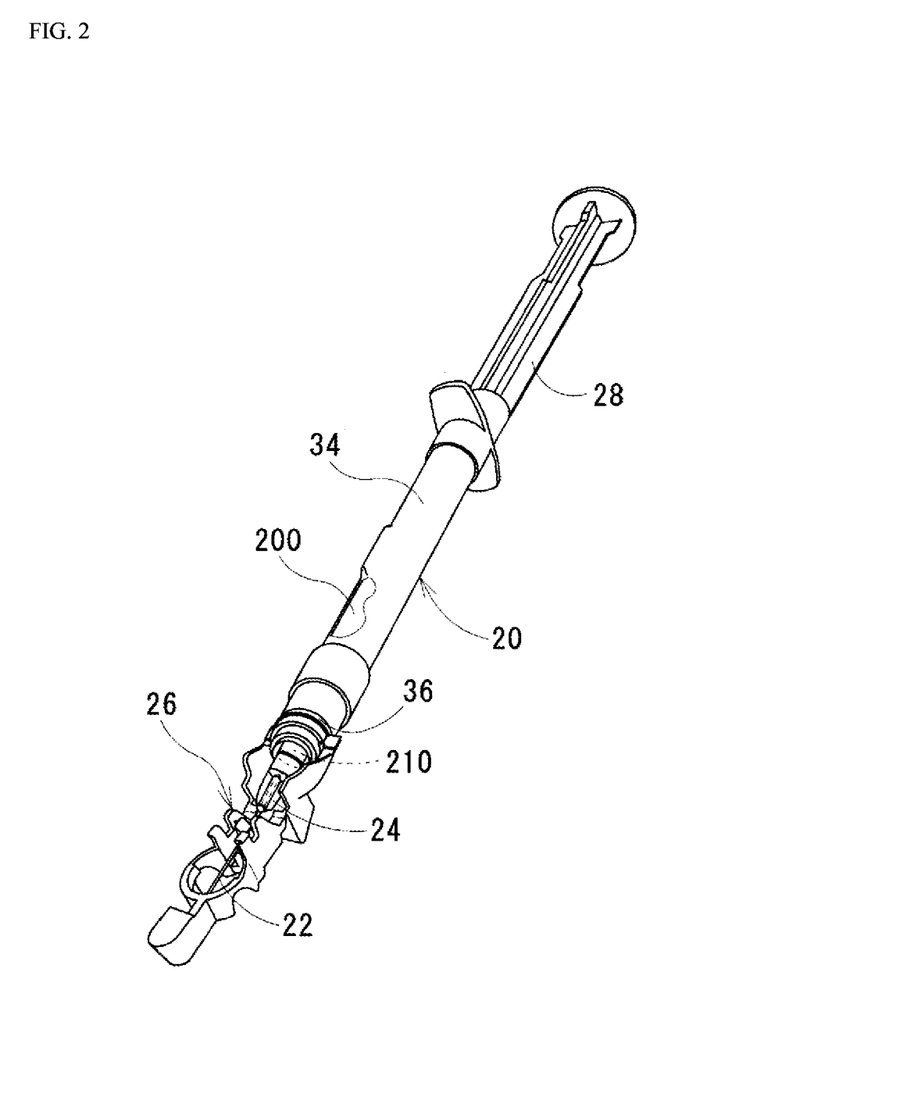
FIG. 2 is a view showing a state of an injection needle cover surrounding an injection needle in the syringe according to the first embodiment of the invention.

FIG. 1 is a view of a syringe according to the present embodiment. FIG. 2 is a view showing a state of an injection needle cover 26 surrounding an injection needle 22 in the syringe according to the embodiment. The syringe according to the embodiment includes a cylinder 20, the injection needle 22, a needle base 24, the injection needle cover 26, a plunger rod 28, and a cylindrical cover 30. Fluid is stored in the cylinder 20. An example of the fluid is liquid. An example of the liquid is a medicine. The injection needle 22 discharges the fluid in the cylinder 20. The needle base 24 connects the injection needle 22 to the cylinder 20. The needle base 24 communicates between an inside of the cylinder 20 and an inside of the injection needle 22. The injection needle cover 26 is attached to the cylinder 20. The injection needle cover 26, when extended as shown in FIG. 2 from a folded state, surrounds the injection needle 22. Before the extension, the cylindrical cover 30 is detached. The plunger rod 28 is inserted into the cylinder 20. As one end (not shown) of the plunger rod 28 goes into the cylinder 20, the fluid and especially the liquid in the cylinder 20 is pushed out. The cylindrical cover 30 covers the injection needle 22 when the injection needle cover 26 is in the folded state shown in FIG. 1.

[Description of Structure of Cylinder]

As shown in FIGS. 1 and 2, the cylinder 20 has an outer cylinder 34 and a cylinder tip 36. The outer cylinder 34 forms a storage space 200. The above-described fluid is stored in the storage space 200. The cylinder tip 36 is formed to protrude from one end of the outer cylinder 34. The needle base 24 is connected to the cylinder tip 36. The cylinder tip 36 forms a communication passage 210. The communication passage 210 communicates between the inside of the injection needle 22 and an inside of the storage space 200.

[Description of Structure of Injection Needle Cover]

Figure 3:
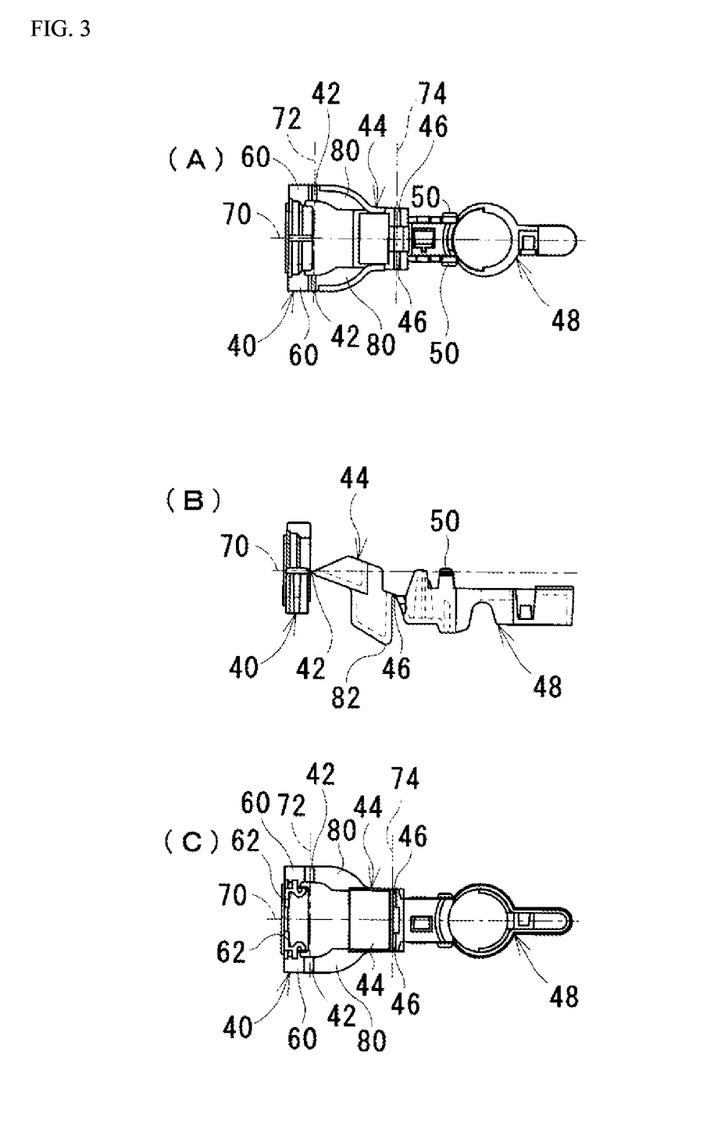
FIGS. 3(A) to 3(C) are external views of the injection needle cover according to the first embodiment of the invention.

FIGS. 3(A) to 3(C) are external views of the injection needle cover 26 according to the embodiment of the invention. FIG. 3(A) is a plan view of the injection needle cover 26 according to the embodiment. FIG. 3(B) is a front view of the injection needle cover 26 according to the embodiment. FIG. 3(C) is a bottom view of the injection needle cover 26 according to the embodiment. The injection needle cover 26 according to the embodiment will be described based on FIGS. 3(A) to 3(C). The injection needle cover 26 according to the embodiment is made of synthetic resin (e.g., polypropylene (PP)). The injection needle cover 26 according to the embodiment includes a base part 40, paired base hinges 42, a fitting space forming part 44, paired connecting hinges 46, an injection needle surrounding part 48, and paired facing connecting parts 50. In the embodiment, these parts are integrated with each other.

In the embodiment, the base part 40 is in an annular shape from opposite ends of which ribs 60 are protruding. In the embodiment, a smooth side face of the base part 40 facing the cylinder tip 36 of the cylinder 20 and the cylinder tip 36 are integrated with each other by welding. In the embodiment, the welding is achieved by rotating the former while pushing the former against the latter. In this way, the base part 40 is fixed to the cylinder tip 36. The base part 40 is fixed in such a manner as to surround the cylinder tip 36. As shown in FIG. 3(C), the base part 40 includes retaining parts 62 as well. The facing connecting parts 50 are connected to the retaining parts 62.

The base hinges 42 are hinges provided to the base part 40. In the embodiment, the base hinges 42 are continuous with the ribs 60 at the opposite ends of the base part 40.

The fitting space forming part 44 is connected to the base part 40 by the base hinges 42. In this way, the fitting space forming part 44 turns about a base axis 72. The base axis 72 passes through the base hinges 42 and is orthogonal to a central axis 70 of the injection needle cover 26 (the central axis 70 passes through a center of the base part 40). The fitting space forming part 44 forms a space. In the space, the needle base 24 and the injection needle surrounding part 48 are to become fitted in the embodiment. The fitting space forming part 44 includes paired arm parts 80 and a moment receiving part 82. The arm parts 80 connect the base hinges 42 and the moment receiving part 82. The paired arm parts 80 are respectively connected to the different base hinges 42. The moment receiving part 82 receives moment about the base axis 72 as a turning center.

The connecting hinges 46 are hinges provided to the fitting space forming part 44 with the moment receiving part 82 interposed therebetween.

The injection needle surrounding part 48 is connected to the fitting space forming part 44 by the paired connecting hinges 46. The injection needle surrounding part 48 turns about a connecting axis 74. The connecting axis 74 passes through the connecting hinges 46 and is parallel to the base axis 72.

In the embodiment, the facing connecting parts 50 are in lug shapes. The facing connecting parts 50 pass through the space formed by the fitting space forming part 44 and get caught on the retaining parts 62 of the base part 40. In this way, the base part 40 and the injection needle surrounding part 48 are connected by the facing connecting parts 50 with the injection needle surrounding part 48 facing the base part 40. As a result, the injection needle cover 26 according to the embodiment takes the form shown in FIG. 1. It is needless to say that the facing connecting parts 50 can be detached from the retaining parts 62.

Figure 4:
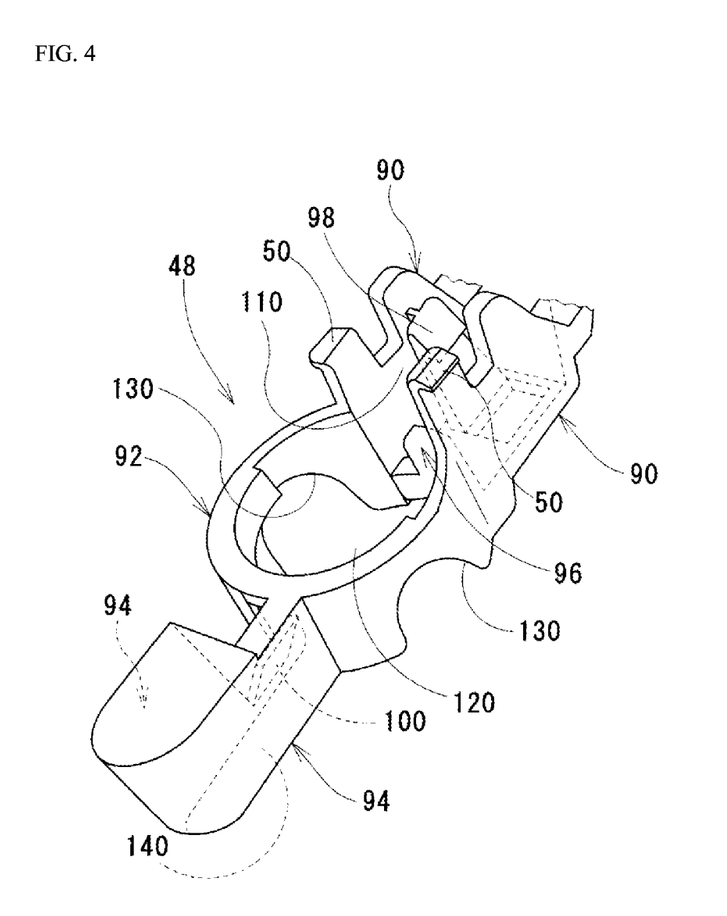
FIG. 4 is a perspective view of an injection needle surrounding part according to the first embodiment of the invention.

FIG. 4 is a perspective view of the injection needle surrounding part 48 according to the embodiment of the invention. The injection needle surrounding part 48 according to the embodiment will be described based on FIG. 4. The injection needle surrounding part 48 according to the embodiment includes paired base-side wall parts 90, a cylinder part 92, paired tip-end-side wall parts 94, an injection needle contact part 96, a hook part 98, and a needle tip end fixing part 100.

The paired base-side wall parts 90 are disposed to face each other. The facing connecting parts 50 are respectively protruding from the base-side wall parts 90. A space between the paired base-side wall parts 90 is a base-side axial space 110. In this way, the paired base-side wall parts 90 form the base-side axial space 110. In the base-side axial space 110, a part of the injection needle 22 is to become fitted.

The cylinder part 92 is continuous with the paired base-side wall parts 90. The cylinder part 92 forms an intra-cylinder space 120. The space surrounded with an inner peripheral face of the cylinder part 92 is the intra-cylinder space 120. As is clear from FIG. 4, the intra-cylinder space 120 communicates with the base-side axial space 110. Paired cutouts 130 are provided to the cylinder part 92.

The paired tip-end-side wall parts 94 are disposed to face each other. The paired tip-end-side wall parts 94 are continuous with the cylinder part 92. A space between the paired tip-end-side wall parts 94 is a tip-end-side axial space 140. In this way, the paired tip-end-side wall parts 94 form the tip-end-side axial space 140. A tip end of the injection needle 22 is to become fitted in the tip-end-side axial space 140. The tip-end-side axial space 140 communicates with the intra-cylinder space 120. The paired tip-end-side wall parts 94 are disposed on an opposite side of the cylinder part 92 from the paired base-side wall parts 90. The paired tip-end-side wall parts 94 are disposed such that the base-side axial space 110 and the tip-end-side axial space 140 are aligned with each other.

In the embodiment, the injection needle contact part 96 is disposed at a position in the base-side axial space 110 which is a boundary between the base-side axial space 110 and the intra-cylinder space 120.

The hook part 98 is protruding into the base-side axial space 110. The needle tip end fixing part 100 is protruding from one of the tip-end-side wall parts 94 into the tip-end-side axial space 140. The hook part 98 and the needle tip end fixing part 100 catch the injection needle 22 when the injection needle 22 becomes fitted into the base-side axial space 110 and the tip-end-side axial space 140.

Figure 5:
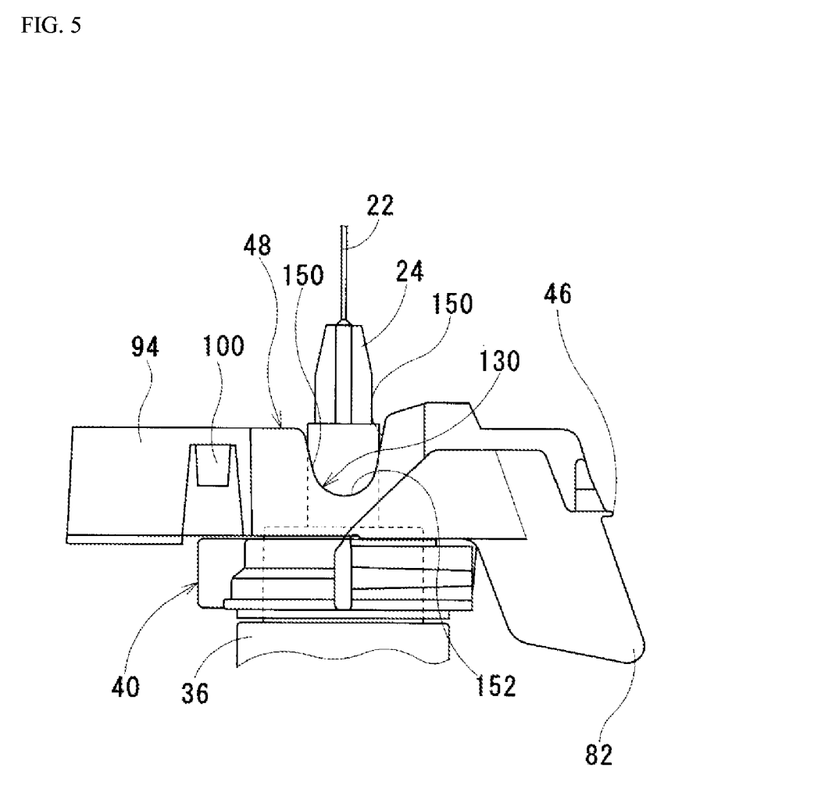
FIG. 5 is an enlarged side view of the injection needle cover according to the first embodiment of the invention.

FIG. 5 is an enlarged side view of the injection needle cover 26 according to the embodiment. Structures of the cutouts 130 provided to the injection needle surrounding part 48 will be described based on FIG. 5. Each of the cutouts 130 has paired cutout inner wall parts 150 and an arcuate bottom part 152.

As is clear from FIG. 5, the paired cutout inner wall parts 150 are inner wall parts of the cutout 130 facing each other. Both of the paired cutout inner wall parts 150 form the single cutout 130. The arcuate bottom part 152 is disposed between the paired cutout inner wall parts 150. The arcuate bottom part 152 is continuous from the paired cutout inner wall parts 150. In other words, one end of the arcuate bottom part 152 is directly connected to one of the paired cutout inner wall parts 150. The other end of the arcuate bottom part 152 is directly connected to the other of the paired cutout inner wall parts 150. Because the cutout 130 has the arcuate bottom part 152, a bottom of the cutout 130 is in an arcuate shape. In the embodiment, a minimum value of a distance between the paired cutout inner wall parts 150 in a direction orthogonal to a central axis of the injection needle 22 is greater than or equal to a maximum value of an opening width of the arcuate bottom part 152 in this direction in the following case. In this case, the base part 40 and the injection needle surrounding part 48 are connected by the facing connecting parts 50 with the injection needle surrounding part 48 facing the base part 40. In the case of the cutout 130 in the embodiment, the distance between the paired cutout inner wall parts 150 reduces toward the arcuate bottom part 152 in such a manner as to meet the above-described requirement. Ends of the cutout inner wall parts 150 are smoothly connected to the ends of the arcuate bottom part 152.

[Description of Method of Using]

Figure 6:
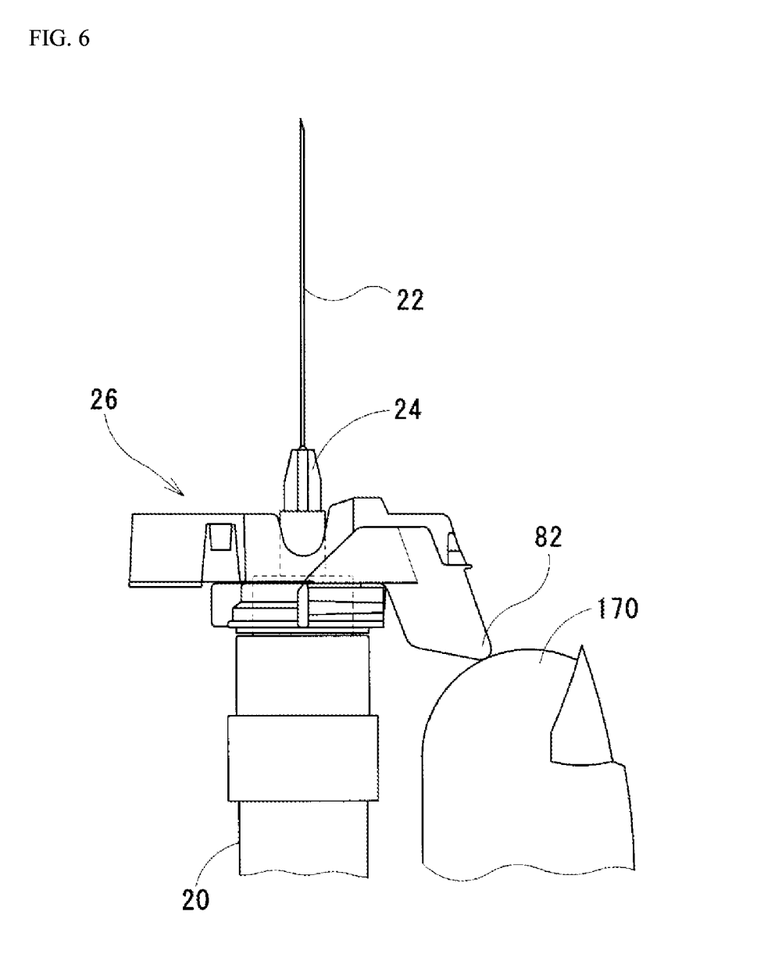
FIG. 6 is a view showing a state of the injection needle cover according to the first embodiment of the invention immediately before operation.
Figure 7:
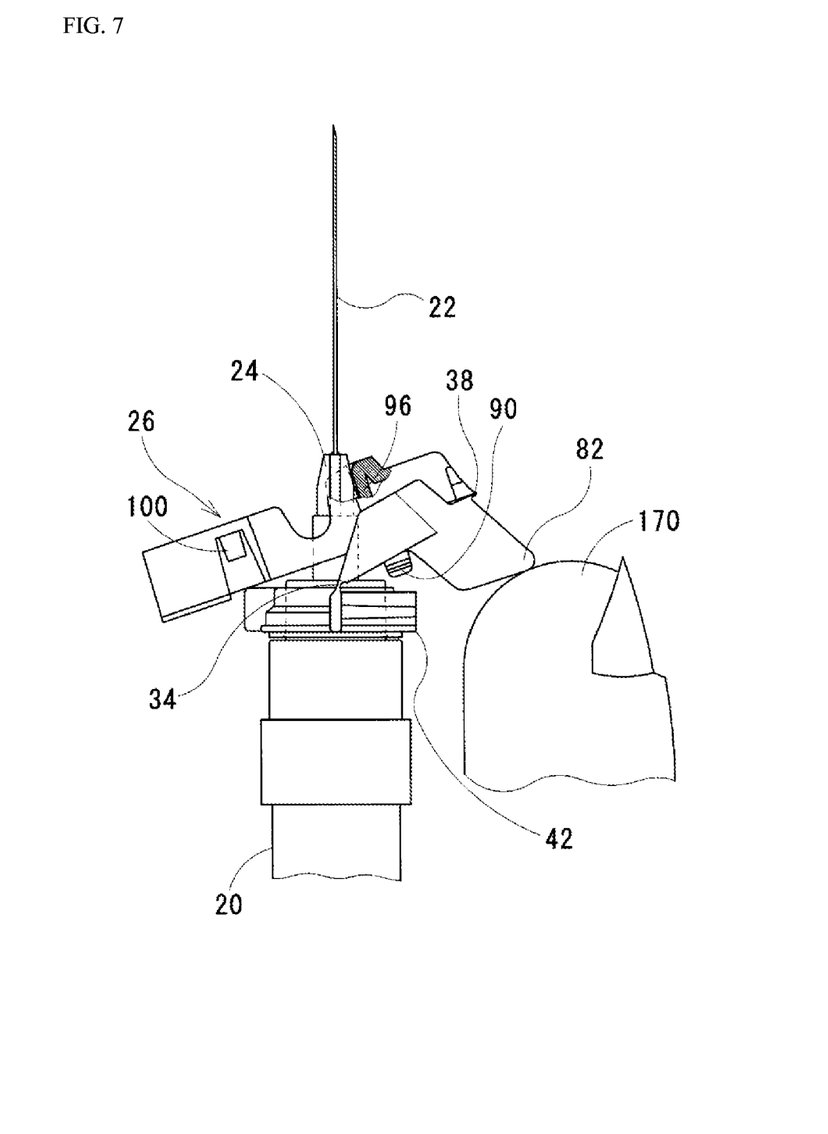
FIG. 7 is a view showing a state of the injection needle cover according to the first embodiment of the invention during the operation.

FIG. 6 is a view showing a state of the injection needle cover 26 according to the embodiment immediately before operation. FIG. 7 is a view showing a state of the injection needle cover 26 according to the embodiment during operation. In this view, a part of the injection needle cover 26 is cut away. The operation of the injection needle cover 26 according to the embodiment will be described based on FIGS. 6 and 7.

First, a user takes the cylindrical cover 30 off the syringe held in his/her hand. If the cylindrical cover 30 is taken off, the user pushes the plunger rod 28. As a result, the liquid in the cylinder 20 is pushed out to the needle base 24.

The user may be looking at the needle base 24 while pushing the plunger rod 28. In the case of the embodiment, the needle base 24 is transparent. Because the needle base 24 is transparent, the user can see the liquid flowing through the needle base 24. If the user is looking at the tip end of the injection needle 22 while the liquid passes through the needle base 24, he/she can stop pushing of the plunger rod 28 at the moment when the liquid squirts out of the tip end. After confirming that the air in the syringe has been pushed out of the syringe in this manner and that the liquid has reached the tip end of the injection needle 22, the user injects the liquid in the syringe into a patient. A specific procedure of the injection is known. Therefore, the procedure will not be described repeatedly here in detail.

After use of the syringe is finished, the user holds the cylinder 20 of the syringe in his/her hand. At this time, the user lightly touches the moment receiving part 82 with his/her thumb 170 as shown in FIG. 6. When the user touches the moment receiving part 82 with his/her thumb 170, the user pushes the moment receiving part 82 in a direction parallel to the injection needle 22 with his/her thumb 170.

As the moment receiving part 82 is pushed, the facing connecting parts 50 caught on the retaining parts 62 are detached from the retaining parts 62. If the facing connecting parts 50 are detached from the retaining parts 62, the folded injection needle cover 26 is naturally extended by resilience of the base hinges 42 and resilience of the connecting hinges 46. The base hinges 42 and the connecting hinges 46 open. As a result, as shown in FIG. 7, the injection needle contact part 96 comes in contact with the needle base 24. At this time, the user keeps pushing the moment receiving part 82 in the direction parallel to the injection needle 22 with his/her thumb 170. As the moment receiving part 82 is kept pushed, the injection needle contact part 96 moves along the needle base 24.

If the injection needle contact part 96 keeps moving along the needle base 24 in this state, the injection needle 22 first becomes fitted into the tip-end-side axial space 140. The tip end part of the injection needle 22 fitted in the tip-end-side axial space 140 gets caught on the needle tip end fixing part 100. Then, the injection needle 22 becomes fitted in the base-side axial space 110. The injection needle 22 fitted in the base-side axial space 110 gets caught on the hook part 98. When a vibration caused when the hook part 98 hooks the tip end part of the injection needle 22 is transmitted to the user's hand, the user stops pushing the moment receiving part 82. At this time, the injection needle cover 26 protects the injection needle 22 as shown in FIG. 2. When the injection needle cover 26 protects the injection needle 22, the user disposes of the syringe with the injection needle cover 26 on it.

Description of Effects of Syringe According to the Embodiment

In the embodiment, the needle base 24 is transparent. The cutouts 130 provided to the injection needle surrounding part 48 make it possible to identify the needle base 24 from outside when the base part 40 and the injection needle surrounding part 48 are connected by the facing connecting part 50 in the folded state of the injection needle cover 26. In this way, it is possible to identify an inside of the needle base 24 from outside. Because the inside of the needle base 24 can be identified from outside, it is possible to make an instant visual identification of entry of the fluid stored in the syringe into the injection needle 22. The instant visual identification of the entry of the fluid makes it possible to instantly stop the operation for pushing out the fluid. Because the operation for pushing out the fluid can be stopped instantly, it is possible to suppress an amount of fluid pushed out from the injection needle 22. As a result, it is possible to suppress the amount of fluid pushed out from the injection needle 22 when confirming whether the air has been pushed out of the injection needle 22.

In the case of the embodiment, each of the cutouts 130 of the injection needle surrounding part 48 has the arcuate bottom part 152. The arcuate bottom parts 152 respectively provided to the cutouts 130, as compared with straight bottoms of cutouts 130, make stress concentration less likely to occur, when the injection needle surrounding part 48 receives a force in such a direction as to narrow openings of the cutouts 130. If the stress concentration becomes less likely to occur, the injection needle surrounding part 48 can withstand a larger force.

In the embodiment, the minimum value of the distance between the paired cutout inner wall parts 150 in the direction (described below) is greater than or equal to the maximum value of the opening width of the arcuate bottom part 152 in this direction. In this way, a view of the needle base 24 is less likely to be obstructed by an edge of the cutout 130 than when the minimum value of the former is smaller than the maximum value of the latter. The direction is orthogonal to the central axis of the injection needle 22 when the base part 40 and the injection needle surrounding part 48 are connected by the facing connecting part 50 in the folded state of the injection needle cover 26. If the view of the needle base 24 is less likely to be obstructed by the edge of the cutout 130, it is easier to visually identify whether the fluid has entered the injection needle 22 than when the view is likely to be obstructed.

Second Embodiment

[Description of Structure of Syringe]

Figure 8:
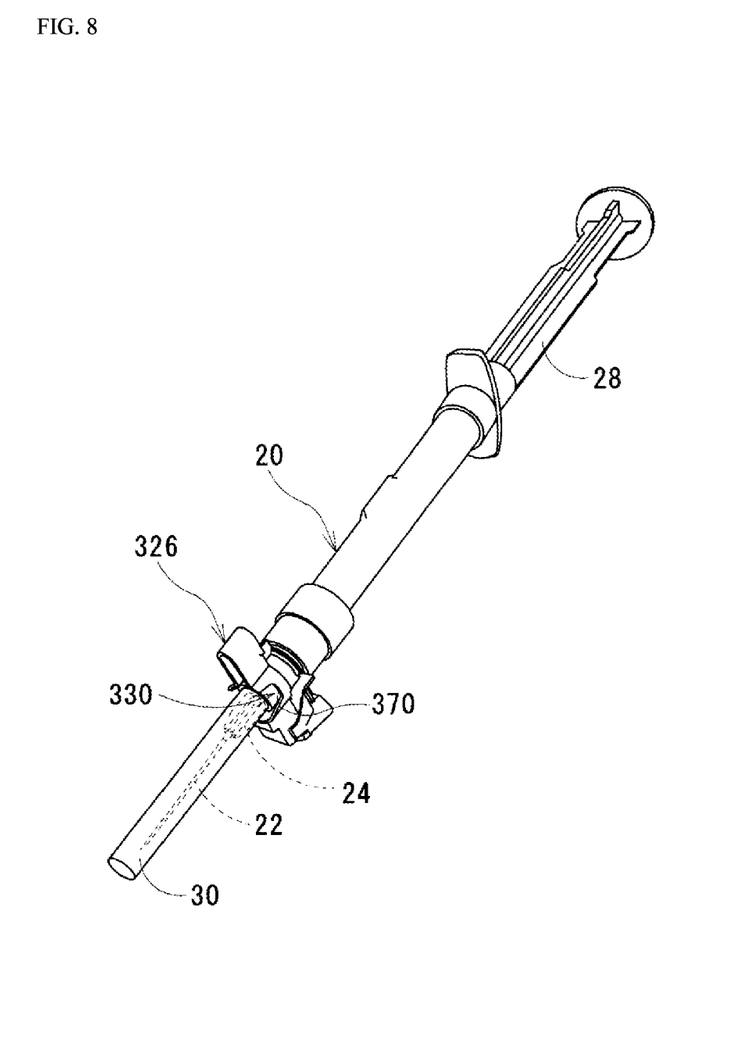
FIG. 8 is a view of a syringe according to a second embodiment of the invention.

FIG. 8 is a view of a syringe according to the present embodiment. The syringe according to the embodiment includes a cylinder 20, an injection needle 22, a needle base 24, an injection needle cover 326, a plunger rod 28, and a cylindrical cover 30. The injection needle cover 326 is attached to the cylinder 20. The injection needle cover 326 is attached to the cylinder 20. The injection needle cover 326, when extended from a folded state, surrounds the injection needle 22. Before the extension, the cylindrical cover 30 is detached.

Figure 9:
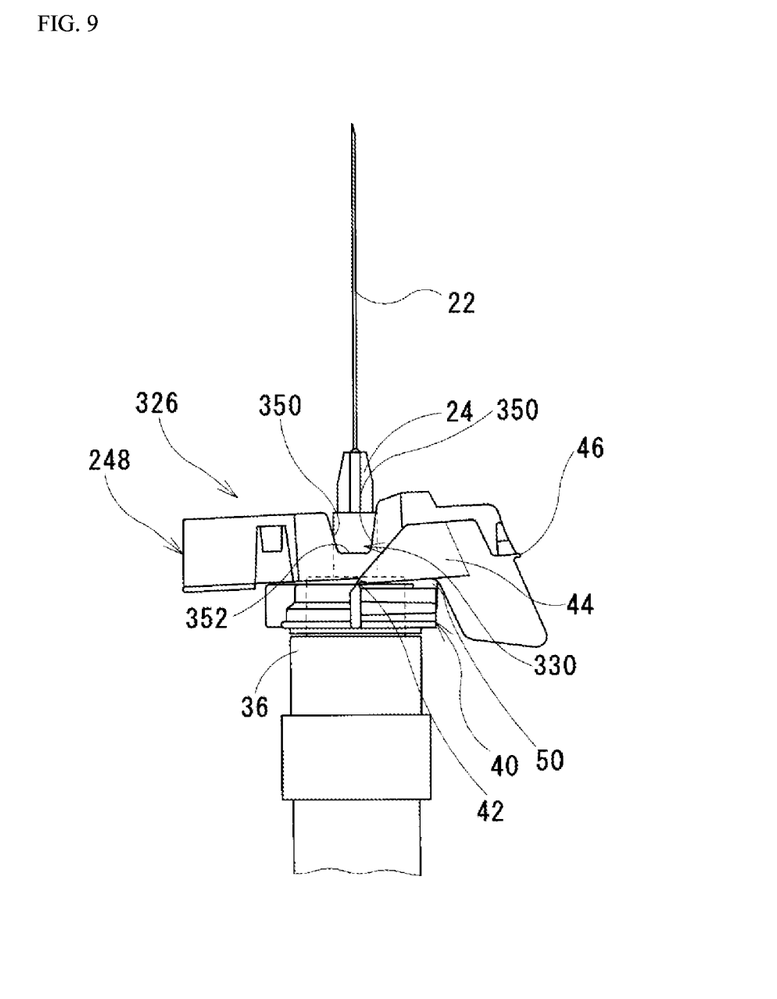
FIG. 9 is an enlarged side view of an injection needle surrounding part according to the second embodiment of the invention.

FIG. 9 is an enlarged side view of the injection needle cover 326 according to the embodiment. A structure of the injection needle cover 326 will be described based on FIG. 9. The injection needle cover 326 according to the embodiment is made of synthetic resin (e.g., polypropylene (PP)). The injection needle cover 326 according to the embodiment includes a base part 40, paired base hinges 42, a fitting space forming part 44, paired connecting hinges 46, an injection needle surrounding part 248, and paired facing connecting parts 50. In the embodiment, these parts are integrated with each other.

A cutout 330 is provided to the injection needle surrounding part 248. The cutout 330 has paired cutout inner wall parts 350 and a linear bottom part 352.

As is clear from FIG. 9, the paired cutout inner wall parts 350 are inner wall parts of the cutout 330 facing each other. Both of the paired cutout inner wall parts 350 form the single cutout 330. The linear bottom part 352 is disposed between the paired cutout inner wall parts 350. Because the cutout 330 has the linear bottom part 352, a bottom of the cutout 330 is in a linear shape from a lateral view. Because the linear bottom part 352 is formed by cutting out a part of the injection needle surrounding part 248, the linear bottom part 352 has an inclined flat face 370.

In the case of the embodiment, an angle of inclination of the flat face 370 meets the following requirement. The requirement is that the flat face 370 extends along a direction orthogonal to a central axis of the injection needle 22 when the base part 40 and the injection needle surrounding part 248 are connected by the facing connecting parts 50 with the injection needle surrounding part 248 facing the base part 40. FIG. 9 shows the injection needle cover 326 meeting the requirement.

Matters other than the above-described matters of the syringe according to the embodiment are similar to those of the syringe according to the first embodiment. Therefore, the procedure will not be described repeatedly here in detail.

[Sensory Testing]

Twenty-five each of the syringe (A) having the injection needle cover according to the invention in FIG. 5 and the syringe (B) having the injection needle cover according to Patent Document 2 were prepared for each of test subjects. The syringes (A) and (B) excluding the injection needle covers had the same structures and were the same as the syringe shown in the first embodiment. The syringes (A), (B) were randomly given to the test subjects and each of the test subjects evaluated the twenty-five each of the syringes (A), (B).

Evaluation Item I: Ease of Handling of Injection Needle Cover

Each of the test subjects touched the moment receiving part of the injection needle cover with his/her thumb and pushed the moment receiving part in the direction parallel to the injection needle to extend the injection needle cover. After handling of the syringes, ease of handling of each of the syringes was evaluated on a three-point scale consisting of the following levels A to C.

A: The cover moved very smoothly.
B: The cover moved to the end while giving a little scratchy feeling.
C: The cover got caught firmly and did not move to the end.

The number of syringes rated as of the respective evaluation levels are shown as percentages of the total number of tests in Table 1.

TABLE 1

| Evaluation level | Syringe A (Injection needle cover in the present invention) | Syringe B (Injection needle cover in Patent Document 2) |
| --- | --- | --- |
| A | 98.7% | 93.3% |
| B | 1.33% | 6.67% |
| C | 0% | 0% |

Evaluation Item II: Visibility

Operation for pushing air out of the injection needle (air removal) of each of the syringes (A), (B) was performed before the injection needle cover was extended and visibility of the needle base in the air removal was evaluated. Each of the test subjects used two each of syringes (A), (B) (out of the twenty-five each of syringes (A), (B) prepared for each of the test subjects) and made the evaluations. The water colored white is contained in each of the syringes and the water moves toward a needle tip by pushing of the plunger rod. With regard to this evaluation item, all of the test subjects evaluated the syringe (A) as having higher visibility in the air removal than the syringe (B). The syringes used for evaluation of the evaluation item II were then used for evaluation of the evaluation item I (the ease of handling of the injection needle cover).

These results showed that the injection needle cover according to the invention maintains the same level or a higher level of ease of handling as or than the injection needle cover in Patent Document 2 and has the higher visibility in the air removal.

Description of Effects of Syringe According to the Embodiment

In the embodiment, the needle base 24 is transparent. The cutout 330 provided to the injection needle surrounding part 248 makes it possible to identify the needle base 24 from outside when the base part 40 and the injection needle surrounding part 248 are connected by the facing connecting part 50 in the folded state of the injection needle cover 326. In this way, it is possible to identify an inside of the needle base 24 from outside. Because the inside of the needle base 24 can be identified from outside, it is possible to make an instant visual identification of entry of the fluid stored in the syringe into the injection needle 22. The instant visual identification of the entry of the fluid makes it possible to instantly stop the operation for pushing out the fluid. Because the operation for pushing out the fluid can be stopped instantly, it is possible to suppress an amount of fluid pushed out from the injection needle 22. As a result, it is possible to suppress the amount of fluid pushed out from the injection needle 22 when confirming whether the air has been pushed out of the injection needle 22.

If the flat face 370 provided to the linear bottom part 352 meets the following requirement, a view of the needle base 24 is less likely to be obstructed by parts close to opposite ends of the linear bottom part 352 than when the flat face 370 does not meet the requirement. The requirement is that the flat face 370 provided to the linear bottom part 352 extends along the direction orthogonal to the central axis of the injection needle 22 when the base part 40 and the injection needle surrounding part 248 are connected by the facing connecting parts 50 with the injection needle surrounding part 248 facing the base part 40. If the view of the needle base 24 is less likely to be obstructed, it is easier to visually identify whether the fluid has entered the injection needle 22 than when the view is likely to be obstructed.

[Description of Variations]

The embodiments disclosed this time are just examples in every respect. The scope of the invention is not restricted by the above-described embodiments. It is needless to say that the invention can be changed in various ways in design without departing from the gist of the invention.

For example, shapes of the cutouts are not restricted to those described above. The injection needle cover is not necessarily made of synthetic resin. The base part, the paired base hinges, the fitting space forming part, the paired connecting hinges, the injection needle surrounding part, and the paired facing connecting parts are not necessarily molded integrally. For example, these members may be formed by connecting a plurality of parts.

DESCRIPTION OF REFERENCE SIGNS

20: Cylinder
22: Injection needle
24: Needle base
26, 326: Injection needle cover 28: Plunger rod
30: Cylindrical cover
34: Outer cylinder
36: Cylinder tip
40: Base part
42: Base hinge
44: Fitting space forming part
46: Connecting hinge
48, 248: Injection needle surrounding part
50: Facing connecting part
60: Rib
62: Retaining part
70: Central axis
72: Base axis
74: Connecting axis
80: Arm part
82: Moment receiving part
90: Base-side wall part
92: Cylinder part
94: Tip-end-side wall part
96: Injection needle contact part
98: Hook part
100: Needle tip end fixing part
110: Base-side axial space
120: Intra-cylinder space
130, 330: Cutout
140: Tip-end-side axial space
150, 350: Cutout inner wall part
152: Arcuate bottom part
170: Thumb
200: Storage space
210: Communication passage
352: Linear bottom part
370: Flat face

The invention claimed is:

1. A syringe comprising:
a cylinder in which fluid is stored;
an injection needle that discharges the fluid;
a needle base that connects the injection needle to the cylinder;
and
an injection needle cover that is attached to the cylinder and, when extended from a folded state, surrounds the injection needle,
wherein the cylinder includes
an outer cylinder that forms a storage space in which the fluid is stored, and
a cylinder tip which is provided to protrude from one end of the outer cylinder, to which the needle base is connected, and which forms a communication passage that is part of or cooperates with the needle base such that the communication passage and needle base jointly allow fluid communication between the injection needle and the cylinder,
the injection needle cover includes
a base part that is fixed to surround the cylinder tip,
a base hinge that is a hinge provided to the base part,
an injection needle surrounding part through which the needle base is inserted and which faces the base part in the folded state of the injection needle cover and which surrounds the injection needle when the injection needle cover is extended, wherein the wall of the injection needle surrounding part surrounds an opening to an intra-cylinder space,
a fitting space forming part that is connected to the base part by the base hinge in such a manner as to turn about a base axis and forms a space in which the injection needle surrounding part is to become fitted, the base axis being an axis orthogonal to a central axis of the injection needle,
a connecting hinge that connects the injection needle surrounding part to the fitting space forming part such that the injection needle surrounding part is movable about a connecting axis which is an axis parallel to the base axis, and
a facing connecting part that connects the base part and the injection needle surrounding part with the injection needle surrounding part facing the base part,
the needle base is transparent or translucent, and
the wall of the injection needle surrounding part has at least one cutout such that the needle base can be identified from outside when the base part and the injection needle surrounding part are connected by the facing connecting part in the folded state of the injection needle cover.

2. The syringe according to claim 1,
wherein the at least one cutout has paired cutout inner wall parts that form each single cutout and face each other, and
an arcuate bottom part that is disposed between the paired cutout inner wall parts and continuous from the paired cutout inner wall parts.

3. The syringe according to claim 2, wherein a minimum value of a distance between the paired cutout inner wall parts in a direction orthogonal to the central axis of the injection needle is greater than or equal to a maximum value of an opening width of the arcuate bottom part in the direction orthogonal to the central axis of the injection needle.

4. The syringe according to claim 1,
wherein the at least one cutout has
paired cutout inner wall parts that form each single cutout and face each other, and
a linear bottom part that is disposed between the paired cutout inner wall parts and inclined when seen from an edge of one of the cutout inner wall parts, and
the linear bottom part has a flat face that extends along a direction orthogonal to the central axis of the injection needle when the base part and the injection needle surrounding part are connected by the facing connecting part with the injection needle surrounding part facing the base part.

* * * * *